US011696898B2

(12) United States Patent
Brosnan

(10) Patent No.: US 11,696,898 B2
(45) Date of Patent: Jul. 11, 2023

(54) HALOGENATED ETHER COMPOUNDS AND METHODS OF INDUCING ANESTHESIA

(71) Applicant: The Regents of the University of California, Oakland, CA (US)

(72) Inventor: Robert J. Brosnan, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/032,371

(22) Filed: Sep. 25, 2020

(65) Prior Publication Data

US 2021/0330604 A1    Oct. 28, 2021

Related U.S. Application Data

(63) Continuation of application No. 15/873,573, filed on Jan. 17, 2018, now abandoned, which is a continuation of application No. 14/730,832, filed on Jun. 4, 2015, now abandoned.

(60) Provisional application No. 62/008,355, filed on Jun. 5, 2014.

(51) Int. Cl.
*A61K 9/00* (2006.01)
*A61K 31/08* (2006.01)

(52) U.S. Cl.
CPC .............. *A61K 31/08* (2013.01); *A61K 9/007* (2013.01); *A61K 9/0019* (2013.01); *A61K 9/0073* (2013.01)

(58) Field of Classification Search
CPC ................ A61K 31/075; A61K 9/0019; A61K 9/0073
See application file for complete search history.

(56) References Cited

U.S. PATENT DOCUMENTS

| 3,314,850 | A | | 4/1967 | Gilbert |
| 3,476,860 | A | | 11/1969 | Croix et al. |
| 3,683,092 | A | | 8/1972 | Regan et al. |
| 3,749,791 | A | | 7/1973 | Terrell et al. |
| 3,749,793 | A | | 7/1973 | Terrell et al. |
| 3,749,794 | A | | 7/1973 | Terrell et al. |
| 3,870,797 | A | | 3/1975 | Holdsworth et al. |
| 3,883,559 | A | | 5/1975 | Burdon et al. |
| 3,897,502 | A | | 7/1975 | Russell et al. |
| 3,943,256 | A | * | 3/1976 | Regan .................... C07C 43/123 514/722 |
| 3,954,893 | A | | 5/1976 | O'Neill et al. |
| 4,017,519 | A | | 4/1977 | Moore et al. |
| 4,060,532 | A | | 11/1977 | Hartmann |
| 4,088,701 | A | | 5/1978 | Siegemund et al. |
| 4,287,124 | A | | 9/1981 | Siegemund et al. |
| 4,334,105 | A | | 6/1982 | Terrell et al. |
| 4,346,246 | A | | 8/1982 | Terrell et al. |
| 4,533,741 | A | | 8/1985 | Squire |
| 4,762,856 | A | | 8/1988 | Terrell |
| 5,488,189 | A | | 1/1996 | Sievert et al. |
| 5,730,894 | A | * | 3/1998 | Minor .................. C11D 7/5086 521/910 |
| 6,218,586 | B1 | | 4/2001 | Takada et al. |
| 7,067,468 | B2 | | 6/2006 | Degroot et al. |
| 8,393,321 | B2 | | 3/2013 | Burns, Jr. et al. |
| 9,381,185 | B2 | | 7/2016 | Brosnan |
| 9,757,353 | B2 | | 9/2017 | Brosnan |
| 10,010,525 | B2 | | 7/2018 | Brosnan |
| 2012/0219596 | A1 | | 8/2012 | Limbach et al. |
| 2014/0018414 | A1 | | 1/2014 | Brosnan |
| 2015/0157596 | A1 | | 6/2015 | Brosnan |
| 2016/0113887 | A1 | | 4/2016 | Brosnan |
| 2016/0296496 | A1 | | 10/2016 | Brosnan |
| 2018/0116997 | A1 | | 5/2018 | Brosnan |

FOREIGN PATENT DOCUMENTS

| AU | 35950/71 A | 5/1973 |
| DE | 2524956 A1 | 12/1976 |
| EP | 0 460 948 A2 | 12/1991 |
| JP | S48-28453 A | 4/1973 |
| JP | S52-39676 A1 | 3/1977 |
| JP | 2018052954 A | 4/2018 |
| WO | 2009029618 A1 | 3/2009 |
| WO | 2014011235 A1 | 1/2014 |
| WO | 2014011815 A2 | 1/2014 |
| WO | 2015187918 A2 | 12/2015 |

OTHER PUBLICATIONS

Burns et al., "An investigation of new fluorine compounds in anaesthesia (1)," Anaesthesia, vol. 16, No. 1, Jan. 1961, 16 pages.
Evans et al., "Fluorocyclohexanes, Part VIII: Lithium Aluminum Hydride Reduction of Decafluorocyclohexene", J. of Chem Soc., 1963, pp. 4828-4834.
Burns et al., "Fluorine compounds in anesthesia (6)," Anaesthesia, Apr. 1964, vol. 19(2), pp. 167-176.
Nath et al., "Studies in vitro on the Effects of 1H,2H,4H(5H)-Octafluorocyclohexane and 1H,4H(2H)-Nonafluorocyclohexane on Enzymes and Organelles," Biochem. J., vol. 114, 1969, pp. 785-792.
Speers et al, "General Anesthetics. 2. Halogenated Methyl Isopropyl Ethers," Journal of Medicinal Chemistry, 1971, vol. 14, No. 7, pp. 593-595.
Cromwell et al., "Forane Uptake, Excretion, and Blood Solubility in Man," Anesthesiology, vol. 35 no. 4, Oct. 1971, pp. 401-408.
Terrell et al., "General Anesthetics. 1. Halogenated Methyl Ethyl Ethers as Anesthetic Agents," Journal of Medicinal Chemistry, 1971, vol. 14, No. 6, pp. 517-519.
Terrell et al., "General Anesthetics. 3. Fluorinated Methyl Ethyl Ethers as Anesthetic Agents," Journal of Medicinal Chemistry, 1972, vol. 15, No. 6, pp. 604-606.
Rudo et al, "Anaesthetic Molecules," Br. J. Anaesth. (1974), 46, 181-189.

(Continued)

*Primary Examiner* — Shobha Kantamneni
(74) *Attorney, Agent, or Firm* — Daniel F. Nesbitt; Nesbitt IP LLC

(57) ABSTRACT

A method of inducing anesthesia in a subject is provided. In some embodiments, the method provides administering to the subject via the respiratory system or via injection, an effective amount of a compound or a mixture of compounds selected from the group consisting of methyl-ethyl ethers, methyl-isopropyl ethers, and methyl-propyl ethers.

18 Claims, No Drawings

(56) References Cited

OTHER PUBLICATIONS

Massuda et al., "Breaking' and formation of hydrogen bonds by proton donor anesthetics," Can. J. Chem., vol. 55, 1977, pp. 3211-3217.
Bagnall et al., "New Inhalation Anaesthetics: I. Fluorinated 1,3-Dioxolane Derivatives," Journal of Fluorine Chemistry, 1977, vol. 9, pp. 359-375.
Bagnall et al., "New Inhalation Anaesthetics: III. Fluorinated Aliphatic Ethers," Journal of Fluorine Chemistry, 1979, vol. 13, pp. 123-140.
Eger et al., "Dioxychlorane: A Challenge to the Correlation of Anesthetic Potency and Lipid Solubility," Anesth. Analg., vol. 60, No. 4, Apr. 1981, pp. 201-203.
Muffler et al., STN Entry—STN Accession No. 1983:125927; Original Publication Date: 1982; 2 pages.
Muffler et al., "Cyclization in the presence of fluoride ions. 2. 4,5-Perfluoro-1,3-dioolanes," Journal of Fluorine Chemistry, 1982; 21(2): pp. 107-132 (English abstract on first page).
Navarrini et al., "A new approach to the synthesis of 2,2-difluoro-1,3-dioxolanes," Journal of Fluorine Chemistry, 1995, vol. 71, pp. 111-117.
Rozov et al., "Asymmetric Synthesis of the Volatile Anesthetic 1,2,2,2-Tetrafluoroethyl Chlorofluoromethyl Ether Using a Stereospecific Decarboxylation of Unusual Stereochemical Outcome," J. Org. Chem., 1995, vol. 60, pp. 1319-1325.
Fang et al., "Anesthetic and Convulsant Properties of Aromatic Compounds and Cycloalkanes: Implications for Mechanisms of Narcosis," Anesth Analg., 1996, vol. 83, pp. 1097-1104.
Patani et al., "Bioisosterism: A Rational Approach in Drug Design," Chem. Rev., 1996, vol. 96, pp. 3147-3176.
Liu et al., "Role of GABA in the actions of ethanol in rats selectively bred for ethanol sensitivity," Pharmacology Biochemistry and Behavior, 1998, vol. 60, No. 4, pp. 793-801.
Eger et al., "Minimum Alveolar Anesthetic Concentration of Fluorinated Alkanols in Rats: Relevance to Theories of Narcosis", Anesthesia and Analgesia, Williams and Wilkins, Baltimore, MD, US, vol. 88, Jan. 1, 1999, pp. 867-876.
Eger et al, "Nonimmobilizers and Transitional Compounds May Produce Convulsions by Two Mechanisms," Anesth Analg 1999; 884-892.
Koblin et al, "Polyhalogenated Methyl Ethyl Ethers: Solubilities and Anesthetic Properties," Anesth Analg 1999; 88:1161-1677.
Hudlicky et al, "Practical preparation of potentially anesthetic fluorinated ethyl methyl ethers by means of bromine trifloride and other methods," Journal of Fluorine Chemistry, 102 (2000) 363-367.
Ming et al., "Differential modulation of GABA- and NMDA-gated currents by ethanol and isoflurane in cultured rat cerebral cortical neurons," Brain Research, 2001, vol. 920, pp. 117-124.
Sako et al, "Critical Parameters and Normal Boiling Temperatures of Five Fluorinated Ethers and Two Fluorinated Ketones," J. Chem. Eng. Data, 2001., vol. 46, pp. 1078-1081.
Williams et al., Foye's Principals of Medicinal Chemistry, 5th Ed., 2002, pp. 59-61.
Altomare et al., "Highly water-soluble derivatives of the anesthetic agent propofol: in vitro and in vivo evaluation of cyclic amino acid esters," European Journal of Pharmaceutical Sciences, 2003, vol. 20, pp. 17-26.
Shiraishi et al., "Effects of Alcohols and Anesthetics on Recombinant Voltage-Gated Na+ Channels", Journal of Pharmacology and Experimental Therapeutics, vol. 309, No. 3, Jan. 1, 2004, pp. 987-994.
Russo et al., "Perfluoro-4-methyl-1,3-dioxole: a new monomer for high-Tg amorphous fluoropolymers," Journal of Fluorine Chemistry, 2004, vol. 125, pp. 73-78.
Leroux et al., "α-Fluorinated Ethers, Thioethers, and Amines: Anomerically Biased Species," Chem. Rev., 2005, vol. 105, pp. 827-856.
Sewell et al., "Determinants of Volatile General Anesthetic Potency: A Preliminary Three-Dimensional Pharmacophore for Halogenated Anesthetics", Anesthesia and Analgesia., vol. 102, No. 3, Mar. 1, 2006, pp. 764-771.
Ludvig et al., "Histological evidence for drug diffusion across the cerebral meninges into the underlying neocortex in rates," Brain Research, 2008, vol. 1188, pp. 228-232.
Abu-Awwad, F., "A QSAR Study of the Activity of Some Fluorinated Anesthetics", Scholars Research Library, Der Pharma Chemica, vol. 2, No. 1, Jan. 1, 2010, pp. 1-13.
Brosnan et al., "Hydrocarbon molar water solubility predicts GABA(A) and NMDA receptor modulation," Anesthesiology, 2011, American Society of Anesthesiologists Annual Meeting, A1597.
Ingolfsson et al., "Alcohol's Effects on Lipid Bilayer Properties," Biophysical Journal, Aug. 2011, vol. 101, pp. 847-855.
Soares et al., "Solubility of Haloether Anesthetics in Human and Animal Blood," Anesthesiology, Jul. 2012, vol. 117(1), pp. 48-55.
International Application No. PCT/US2013/031668, International Search Report and Written Opinion dated Jun. 28, 2013, 11 pages.
International Application No. PCT/US2013/049985, International Search Report and Written Opinion dated Sep. 27, 2013, 5 pages.
Brosnan et al., "Hydrocarbon molar water solubility predicts NMDA vs. GABA(A) receptor modulation," BMC Pharmacology and Toxicology, Nov. 2014, vol. 15, p. 62, 13 pages.
Extended European Search Report, European Application No. 13816414. 0, dated Jan. 5, 2016, 10 pages.
International Application No. PCT/US2015/034137, International Search Report and Written Opinion dated Jan. 26, 2016, 10 pages.
U.S. Appl. No. 14/730,832, Restriction Requirement dated Sep. 8, 2016, 6 pages.
U.S. Appl. No. 14/730,832, Final Office Action dated Jul. 19, 2017, 11 pages.
U.S. Appl. No. 14/730,832, Non-Final Office Action dated Feb. 6, 2017, 14 pages.
European Patent Application No. 13816414.0, Office Action dated Mar. 14, 2018, 6 pages.
European Patent Application No. 18151918.2, Extended European Search Report dated Apr. 20, 2018, 11 pages.
U.S. Appl. No. 17/087,365, filed Nov. 2, 2020, Brosnan.
First Office Action dated Aug. 9, 2022 in related Japanese Application No. 2021-114241 filed Jul. 9, 2021 (3 pages) with JPO machine translation (4 pages).

\* cited by examiner

HALOGENATED ETHER COMPOUNDS AND METHODS OF INDUCING ANESTHESIA

CROSS-REFERENCE TO RELATED APPLICATIONS

This application is a continuation of U.S. patent application Ser. No. 15/873,573 filed Jan. 17, 2018, which is a continuation of U.S. patent application Ser. No. 14/730,832 filed Jun. 4, 2015, which claims the benefit of U.S. Provisional Application No. 62/008,355, filed Jun. 5, 2014, the disclosures of which are hereby incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. GM092821 awarded by the National Institutes of Health. The Government has certain rights in this invention.

FIELD OF THE INVENTION

The present invention provides methods for inducing anesthesia or sedation in a subject by administering via the respiratory pathways (e.g., via inhalational or pulmonary delivery) an effective amount of an anesthetic compound described herein.

BACKGROUND OF THE INVENTION

Molecular Mechanisms of Anesthetic Action

All general anesthetics in common clinical use modulate either three-transmembrane (TM3) ion channels (e.g., NMDA receptors), four-transmembrane (TM4) ion channels (e.g., $GABA_A$ receptors), or members of both ion channel superfamilies. Sonner, et al., Anesth Analg (2003) 97:718-40. For example, many structurally unrelated inhaled anesthetics potentiate $GABA_A$ currents and inhibit NMDA currents. But why should a diverse group of compounds all modulate unrelated ion channels? A highly specific "induced fit" model between protein and ligand, as proposed for enzyme-substrate binding, (Koshland, Proc Natl Acad Sci USA 1958; 44: 98-104) is problematic since it implies the conservation of specific binding sites across non-homologous proteins to compounds (i.e., anesthetics) not found in nature. Sonner, Anesth Analg (2008) 107: 849-54. Moreover, promiscuous anesthetic actions on disparate receptors typically occurs at drug concentrations 50-200 times the median effective concentration (EC50) at which modulation of a single receptor class typically occurs, such as with etomidate agonism of $GABA_A$ receptors (Tomlin et al., Anesthesiology (1998) 88: 708-17; Hill-Venning, et al., Br J Pharmacol (1997) 120: 749-56; Belelli, et al., Br J Pharmacol (1996) 118: 563-76; Quast, et al., J Neurochem (1983) 41:418-25; and Franks, Br J Pharmacol 2006; 147 Suppl 1: S72-81) or dizocilpine (MK-801) antagonism of NMDA receptors. Wong, et al., Proc Natl Acad Sci USA (1986) 83: 7104-8; Ransom, et al., Brain Res (1988) 444: 25-32; and Sircar, et al., Brain Res (1987) 435: 235-40. It is unknown what molecular properties confer specificity for a single receptor (or members of a single receptor superfamily) and what properties allow other anesthetics to modulate multiple unrelated receptors. However, since ion channel modulation is important to conferring desirable anesthetic efficacy—as well as undesirable drug side effects—it is desirable to know what factors influence anesthetic receptor specificity in order to develop new and safer agents.

Anesthetics and Specific Ion Channel Targets

General anesthetics mediate central nervous system depression through actions on cell membrane receptors and channels which have a net hyperpolarizing effect on neurons. Sonner, et al., Anesth Analg (2003) 97:718-40; Grasshoff, et al., Eur J Anaesthesiol (2005) 22: 467-70; Franks, Br J Pharmacol (2006) 147 Suppl 1: S72-81; 33; Hemmings, et al., Trends Pharmacol Sci (2005) 26: 503-10; and Forman, et al., Int Anesthesiol Clin (2008) 46: 43-53. Although anesthetics partition into cell membranes as a function of lipid solubility, it is through competitive protein binding that these agents most likely produce anesthetic effects. In fact, general anesthetics have been shown to competitively inhibit functions of membrane-free enzymes (Franks, et al., Nature (1984) 310: 599-601), indicating that the lipid phase is not essential for anesthetic modulation of protein function. Specific high-affinity binding sites have been identified for some of these anesthetics. For example, propofol (Jewett, et al., Anesthesiology (1992) 77: 1148-54; Bieda, et al., J Neurophysiol (2004) 92: 1658-67; Peduto, et al., Anesthesiology 1991; 75: 1000-9; Sonner, et al, Anesth Analg (2003) 96: 706-12; and Dong et al., Anesth Analg (2002) 95: 907-14), etomidate (Flood, et al., Anesthesiology (2000) 92: 1418-25; Zhong, et al., Anesthesiology 2008; 108: 103-12; O'Meara, et al., Neuroreport (2004) 15: 1653-6), and thiopental (Jewett, et al., Anesthesiology (1992) 77: 1148-54; Bieda, et al, J Neurophysiol (2004) 92: 1658-67; Yang, et al., Anesth Analg (2006) 102: 1114-20) all potently potentiate $GABA_A$ receptor currents, and their anesthetic effects are potently antagonized or prevented by $GABA_A$ receptor antagonists, such as pictotoxin or bicuculline. Ketamine produces anesthesia largely (but not entirely) through its antagonism of NMDA receptors. Harrison et al., Br J Pharmacol (1985) 84: 381-91; Yamamura, et al., Anesthesiology (1990) 72: 704-10; and Kelland, et al., Physiol Behav (1993) 54: 547-54. Dexmedetomidine is a specific α2 adrenoreceptor agonist that is antagonized by specific α2 adrenoreceptor antagonists, such as atipamezole. Doze, et al., Anesthesiology (1989) 71: 75-9; Karhuvaara, et al., Br J Clin Pharmacol (1991) 31: 160-5; and Correa-Sales, et al., Anesthesiology (1992) 76: 948-52. It is probably not by coincidence that anesthetics for which a single receptor contributes to most or all of the anesthetic effect also have low aqueous $EC_{50}$ values (see, Table 1).

TABLE 1

Aqueous phase $EC_{50}$ for several anesthetics.

| Anesthetic | Aqueous $EC_{50}$ (μM) | Species | Reference |
| --- | --- | --- | --- |
| Propofol | 2 | Rat | Tonner et al., Anesthesiology (1992) 77: 926-31 |
| Ketamine | 2 | Human | Flood, et al., Anesthesiology (2000) 92: 1418-25 |
| Etomidate | 3 | Tadpole | Tomlin, et al., Anesthesiology (1998) 88: 708-17 |

TABLE 1-continued

Aqueous phase $EC_{50}$ for several anesthetics.

| Anesthetic | Aqueous $EC_{50}$ (µM) | Species | Reference |
|---|---|---|---|
| Dexmedetomidine | 7 | Tadpole | Tonner, et al., *Anesth Analg* (1997) 84: 618-22 |
| Thiopental | 25 | Human | Flood, et al., *Anesthesiology* (2000) 92: 1418-25 |
| Methoxyflurane | 210 | Tadpole | Franks, et al., *Br J Anaesth* (1993) 71: 65-76 |
| Halothane | 230 | Tadpole | Franks, et al., *Br J Anaesth* (1993) 71: 65-76 |
| Isoflurane | 290 | Tadpole | Franks, et al., *Br J Anaesth* (1993) 71: 65-76 |
| Chloroform | 1300 | Tadpole | Franks, et al., *Br J Anaesth* (1993) 71: 65-76 |
| Diethyl ether | 25000 | Tadpole | Franks, et al., *Br J Anaesth* (1993) 71: 65-76 |

Ion channel mutations, either in vitro or in vivo, dramatically alter anesthetic sensitivity, not only for the very potent and specific agents, but also for the inhaled anesthetics. Several mutations in the $GABA_A$ (Hara, et al., *Anesthesiology* 2002; 97: 1512-20; Jenkins, et al., *J Neurosci* 2001; 21: RC136; Krasowski, et al., *Mol Pharmacol* 1998; 53: 530-8; Scheller, et al., *Anesthesiology* 2001; 95: 123-31; Nishikawa, et al., *Neuropharmacology* 2002; 42: 337-45; Jenkins, et al., *Neuropharmacology* 2002; 43: 669-78; Jurd, et al., *FASEB J* 2003; 17: 250-2; Kash, et al., *Brain Res* 2003; 960: 36-41; Borghese, et al., *J Pharmacol Exp Ther* 2006; 319: 208-18; Drexler, et al., *Anesthesiology* 2006; 105: 297-304) or NMDA (Ogata, et al., *J Pharmacol Exp Ther* (2006) 318: 434-43; Dickinson, et al., *Anesthesiology* 2007; 107: 756-67) receptor can decrease responses to isoflurane, halothane, and other volatile anesthetics. Although mutations that render receptors insensitive to anesthetics could suggest a single site that is responsible for binding a specific drug, it need not be the case. Most of these mutations are believed to reside near lipid-water interfaces, either in amphiphilic protein pockets (Bertaccini et al., *Anesth Analg* (2007) 104: 318-24; Franks, et al., *Nat Rev Neurosci* (2008) 9: 370-86) or near the outer lipid membrane. It is possible that an anesthetic could be excluded from its protein interaction site because of size. However, it is also possible that the mutation substantially increases (but does not entirely exclude) the number of "non-specific" low-affinity anesthetic-protein interactions necessary to modulate the receptor. In this case, modulation of the mutant receptor will either only occur at anesthetic concentrations in excess of the wild-type minimum alveolar concentration (MAC) (Eger, et al., *Anesthesiology* (1965) 26: 756-63) or, if the drug is insufficiently soluble at the active site to allow a sufficient number of "non-specific" interactions with the mutant protein, no receptor modulation will be possible even at saturating aqueous drug concentrations.

Another argument for specific "induced fit" binding sites on ion channels is the "cut-off" effect. For example, increasing the carbon chain length of an alkanol increases lipid solubility and anesthetic potency, as predicted by the Meyer-Overton hypothesis (Overton C E: Studies of Narcosis. London, Chapman and Hall, 1991), until a 12-carbon chain length (dodecanol) is reached (Alifimoff, et al., *Br J Pharmacol* (1989) 96: 9-16). Alkanols with a longer chain length were not anesthetics (hence, a "cut-off" effect at C=13 carbons). However, the hydrocarbon chain length needed to reach the cut-off effect is C=9 for alkanes (Liu, et al., *Anesth Analg* (1993) 77: 12-8), C=2 for perfluorinated alkanes (Liu, et al., *Anesth Analg* (1994) 79: 238-44), and C=3 for perfluorinated methyl ethyl ethers (Koblin, et al., *Anesth Analg* (1999) 88: 1161-7). If size is essential to access a specific anesthetic binding site, then why is the "cut-off" chain length not constant? At the cellular level, straight-chain alcohols can maximally inhibit NMDA receptor function up to octanol with complete cut-off at C=10. But straight-chain 1, Ω-diols maximally inhibit NMDA receptors up to decanol, with complete cut-off not observed until C=16 (Peoples, et al., *Mol Pharmacol* (2002) 61: 169-76). Increasing hydrocarbon chain length does not only increase molecular volume, but also decreases water solubility. The cut-off effect therefore refers to a minimum water solubility necessary to produce an effect, rather than a maximum molecular size.

At the tens of micromolar concentrations or less, anesthetics most likely exert their effects on ion channels by specific binding to relatively high-affinity sites on proteins to induce a conformational change that alters ion conductance, either alone or in the presence of another endogenous ligand. However, these agents can still interact with other receptors (or the same receptor at different sites) if present in higher concentrations. For example, assume that two dissimilar receptors (R1 and R2) each can exert an anesthetic effect. Assuming that efficacy of a drug at R1=1, that R1 is able to produce a full anesthetic effect in isolation, and that the EC99 of R1 is less than the EC1 of R2, then this drug will produce anesthesia by selectively modulating R1. However, if any of these assumptions is not true, then some contribution of R2 will be required to produce an anesthetic effect (Figure 1).

Many injectable anesthetics seem to follow the example described above. Propofol is a positive modulator of $GABA_A$ receptor currents with an $EC_{50}$ around 60 µM (Hill-Venning, et al., *Br J Pharmacol* (1997) 120: 749-56; Prince, et al., *Biochem Pharmacol* (1992) 44: 1297-302; Orser, et al., *J Neurosci* (1994) 14: 7747-60; Reynolds, et al., *Eur J Pharmacol* (1996) 314: 151-6), and propofol is believed to mediate the majority of its anesthetic effects through potentiation of $GABA_A$ currents (Sonner, et al, *Anesth Analg* (2003) 96: 706-12). However, propofol also inhibits currents from the unrelated NMDA receptor with an $IC_{50}$ of 160 µM (Orser, et al., *Br J Pharmacol* (1995) 116: 1761-8). Ketamine produces anesthesia largely through antagonism of NMDA receptors, which it inhibits with an $IC_{50}$ of 14 µM (Liu, et al., *Anesth Analg* (2001) 92: 1173-81), although 365 µM ketamine also increases unrelated 4 transmembrane $GABA_A$ receptor currents by 56% (Lin, et al., *J Pharmacol Exp Ther* (1992) 263: 569-78). In these cases, it seems plausible that 2 different types of interactions (for high- vs. low-affinity responses) could occur on a single receptor to produce the same qualitative effect. In contrast, volatile inhaled anesthetics generally have little or no effect on $GABA_A$ and NMDA receptors at aqueous phase concentrations<50 µM (Lin, et al., *J Pharmacol Exp Ther* (1992) 263: 569-78; Moody, et al., *Brain Res* (1993) 615: 101-6; Harris, et al., *J Pharmacol Exp Ther* (1993) 265: 1392-8; Jones, et al., *J Physiol* (1992) 449: 279-93; Hall, et al., *Br J*

*Pharmacol* (1994) 112: 906-10). It is possible that these agents are not specific ligands for any anesthetic-sensitive receptor that is relevant to immobility; thus they may rely only on nonspecific protein-ligand interactions that, in turn, may be reflected in the higher aqueous phase concentrations of these agents required for anesthesia (Table 1).

Halogenated Methyl-Alkyl Ethers

The conventional methyl-alkyl ether anesthetics are well known and include enflurane, isoflurane, desflurane, and sevoflurane. The identification and selection of suitable alkyl-ethyl ether compounds as anesthetics, though, required a long, tedious, and often unsuccessful path of identifying, synthesizing, testing, and characterizing medicinal properties and testing a larger series of compound candidates by little more than trial and error, without any clear guidelines or "blaze marks" to aid the research in the selection of candidates. Over 700 different compounds were synthesized, characterized and tested during the 1960's and 1970's, without a guideline or method to predict relevant anesthetic-sensitive receptor activity or selectivity. See, Burns W B, Eger E I, 2nd: Ross C. Terrell, PhD, an anesthetic pioneer. Anesth Analg 2011; 113: 387-9; and Terrell R C: The invention and development of enflurane, isoflurane, sevoflurane, and desflurane. Anesthesiology 2008; 108: 531-3.

Despite these past efforts and the many, predominantly disappointing outcomes, many novel or untested ether anesthetics may still be effective, and given unlimited money, time, and personnel, might be discovered and developed through the same trial and error. However, such an approach is inefficient and generally impractical. Without a guideline or testing means for screening through such compounds to identify the more likely successful candidates, new novel or untested anesthetic agents would likely remain unidentified indefinitely.

SUMMARY OF THE INVENTION

In one aspect, the present invention provides methods, and compounds for use in the methods, of inducing anesthesia in a subject. In some embodiments, the methods, and compounds for use in the methods, comprise administering to the subject via the respiratory system an effective amount of a compound or a mixture of compounds selected from the group consisting of halogenated methyl-ethyl ethers, halogenated methyl-isopropyl ethers, and halogenated methyl-propyl ethers.

In another aspect, the present invention provides a method for inducing anesthesia in a subject, comprising administering to the subject via the respiratory system an effective amount of ethane, 1-bromo-1,1,2-trifluoro-2-(trifluoromethoxy)- (CAS #2356-55-0).

In another aspect, the present invention provides a compound for use in a method for inducing anesthesia in a subject, which method comprises administering to the subject via the respiratory system an effective amount of ethane, 1-bromo-1,1,2-trifluoro-2-(trifluoromethoxy)- (CAS #2356-55-0).

In certain embodiments, the subject is a mammal, and can include a human.

In certain embodiments, the halogenated methyl-ethyl ether is selected from the group consisting of: Ethane, 1-(chlorodifluoromethoxy)-1,1,2,2,2-pentafluoro- (CAS #276640-96-1); Ethane, 2-bromo-1,1,1-trifluoro-2-(trifluoromethoxy)- (CAS #84011-04-1); Ethane, 1-bromo-1,2,2-trifluoro-1-(trifluoromethoxy)- (CAS #885275-60-5); Ethane, 2-bromo-1,1,2-trifluoro-1-(trifluoromethoxy)- (CAS #84011-03-0); Ethane, 1-bromo-1,1,2-trifluoro-2-(trifluoromethoxy)- (CAS #2356-55-0); Ethane, 2-chloro-1,1,2-trifluoro-1-(trifluoromethoxy)- (CAS #879885-11-7); Ethane, 2-chloro-1,1,1-trifluoro-2-(trifluoromethoxy)- (CAS #94720-92-0); Ethane, 1-chloro-2-(difluoromethoxy)-1,1,2,2-tetrafluoro- (CAS #32778-12-4); Ethane, 1-chloro-1,1,2-trifluoro-2-(trifluoromethoxy)-(CAS #2356-59-4); Ethane, 1-chloro-1-(difluoromethoxy)-1,2,2,2-tetrafluoro- (CAS #57041-64-2); Ethane, 2-(chlorodifluoromethoxy)-1,1,1,2-tetrafluoro- (CAS #172103-16-1); Ethane, 2-(chlorodifluoromethoxy)-1,1,1,2-tetrafluoro-, (S)-(9CI) (CAS #167072-93-7); Ethane, 2-(chlorodifluoromethoxy)-1,1,1,2-tetrafluoro-, (R)-(9CI) (CAS #161893-84-1); Ethane, 1-(chlorodifluoromethoxy)-1,1,2,2-tetrafluoro- (CAS #37031-51-9); Ethane, 2-chloro-1,1-difluoro-1-(trifluoromethoxy)- (CAS #25957-33-9); Ethane, 1-chloro-1,1,2,2-tetrafluoro-2-(fluoromethoxy)- (CAS #53997-65-2); Ethane, 1-chloro-1,1-difluoro-2-(trifluoromethoxy)- (CAS #1645-80-3); Ethane, 1-chloro-1,2-difluoro-2-(trifluoromethoxy)-, (R*,S*)-(9CI) (CAS #84011-29-0); Ethane, 1-chloro-1,2-difluoro-2-(trifluoromethoxy)-, (R*,R*)-(9CI) (CAS #84011-28-9); Ethane, 1-chloro-1,2-difluoro-2-(trifluoromethoxy)-(CAS #54362-39-9); Ethane, 1-chloro-2,2-difluoro-1-(trifluoromethoxy)- (CAS #33445-33-9); Ethane, 2-(chlorodifluoromethoxy)-1,1,1-trifluoro- (CAS #33018-78-9); and mixtures thereof.

In another embodiment, the halogenated methyl-ethyl ether is selected from the group consisting of: Ethane, 1-(chlorodifluoromethoxy)-1,1,2,2,2-pentafluoro- (CAS # 276640-96-1); Ethane, 2-bromo-1,1,1-trifluoro-2-(trifluoromethoxy)- (CAS #84011-04-1); Ethane, 1-bromo-1,2,2-trifluoro-1-(trifluoromethoxy)- (CAS #885275-60-5); Ethane, 2-bromo-1,1,2-trifluoro-1-(trifluoromethoxy)- (CAS #84011-03-0); Ethane, 1-bromo-1,1,2-trifluoro-2-(trifluoromethoxy)- (CAS #2356-55-0); Ethane, 2-chloro-1,1,2-trifluoro-1-(trifluoromethoxy)- (CAS #879885-11-7); Ethane, 2-chloro-1,1,1-trifluoro-2-(trifluoromethoxy)- (CAS #94720-92-0); Ethane, 1-chloro-1,1,2-trifluoro-2-(trifluoromethoxy)- (CAS #2356-59-4); Ethane, 1-chloro-1,1-difluoro-2-(trifluoromethoxy)-(CAS #1645-80-3); Ethane, 1-chloro-1,2-difluoro-2-(trifluoromethoxy)-, (R*,S*)-(9CI) (CAS #84011-29-0); Ethane, 1-chloro-1,2-difluoro-2-(trifluoromethoxy)-, (R*,R*)-(9CI) (CAS #84011-28-9); Ethane, 1-chloro-1,2-difluoro-2-(trifluoromethoxy)- (CAS #54362-39-9); Ethane, 1-chloro-2,2-difluoro-1-(trifluoromethoxy)- (CAS #33445-33-9); and mixtures thereof.

In another embodiment, a halogenated methyl-ethyl ether described herein is a brominated methyl-ethyl ether.

In certain embodiments, the halogenated methyl-isopropyl ether is selected from the group consisting of: Propane, 1-chloro-1,1,2,3,3,3-hexafluoro-2-(trifluoromethoxy)- (CAS #41255-97-4); Propane, 1,1,1,2,3,3,3-heptafluoro-2-(trifluoromethoxy)- (CAS #60901-74-8); Propane, 1,1,1,3,3,3-hexafluoro-2-(trifluoromethoxy)- (CAS #162401-05-0); Propane, 2-(difluoromethoxy)-1,1,1,2,3,3,3-heptafluoro- (CAS #57041-60-8); Propane, 1,1,1,2,3,3,3-heptafluoro-2-(fluoromethoxy)- (CAS #57041-59-5); Propane, 2-(difluoromethoxy)-1,1,1,3,3,3-hexafluoro- (CAS #26103-08-2); Propane, 2-(difluoromethoxy)-1,1,1,2,3,3-hexafluoro- (CAS #233258-12-3); Propane, 1,1,1,2,3,3,3-heptafluoro-2-methoxy- (CAS #22052-84-2); Propane, 1,1,1,3,3,3-hexafluoro-2-methoxy- (CAS #13171-18-1); Propane, 1,1,2-trifluoro-2-(trifluoromethoxy)- (CAS #1219442-00-8); Propane, 2-(difluoromethoxy)-1,1,1,2-tetrafluoro- (CAS #32793-57-0); and mixtures thereof.

In certain embodiments, the halogenated methyl-isopropyl ether is selected from the group consisting of: Propane, 1-chloro-1,1,2,3,3,3-hexafluoro-2-(trifluoromethoxy)- (CAS

41255-97-4); Propane, 1,1,1,2,3,3,3-heptafluoro-2-(trifluoromethoxy)- (CAS #60901-74-8); Propane, 1,1,1,3,3,3-hexafluoro-2-(trifluoromethoxy)- (CAS #162401-05-0); Propane, 2-(difluoromethoxy)-1,1,1,2,3,3-hexafluoro- (CAS #233258-12-3); and mixtures thereof.

In certain embodiments, the halogenated methyl-propyl ether is selected from the group consisting of: Propane, 1,1,2,2,3,3-hexafluoro-1-methoxy- (CAS #160620-20-2); Propane, 1,1,1,2,2,3-hexafluoro-3-methoxy- (CAS #123202-00-6); Propane, 1,1,1,2,3,3-hexafluoro-3-(fluoromethoxy)- (CAS #60598-14-3); Propane, 3-(difluoromethoxy)-1,1,1,2,2-pentafluoro- (CAS #56860-81-2); Propane, 1,1,1,2,2-pentafluoro-3-(fluoromethoxy)- (CAS #1515-13-5); and mixtures thereof.

In an aspect of the invention, a halogenated methyl-alkyl ether compound useful in a method of the present invention has a molar water solubility of equal to or greater than about 0.016 mM that is sufficient to potentiate $GABA_A$ receptors. Preferably, a methyl-alkyl ether compound useful in a method of the present invention has a molar water solubility equal to or greater than about 2.4 mM.

In another aspect of the invention, a halogenated methyl-alkyl ether compound useful in a method of the present invention, which does not modulate or inhibit NMDA receptor at a saturated aqueous phase concentration, can have a molar water solubility (calculated) of less than about 11 mM, and more typically less than about 5.7 mM.

In some embodiments, the subject is a mammal. In some embodiments, the subject is a human.

In some embodiments, the step of inducing anesthesia includes inducing a state selected from the group consisting of analgesia, tranquilization, sedation, amnesia, a hypnotic state, and a state of insensitivity to noxious stimulation.

In another aspect, the invention provides a method of inducing anesthesia in a subject, comprising administering via injection, including intravenously, subcutaneously, intramuscularly, perineurally or transdermally, to the subject, an effective amount of a compound or a mixture of compounds selected from the group consisting of methyl-ethyl ethers, methyl-isopropyl ethers, and methyl-propyl ethers.

In a further aspect, the invention provides a method of selecting a methyl-alkyl ether anesthetic that preferentially activates or potentiates $GABA_A$ receptors without inhibiting NMDA receptors, the method comprising: a) determining a molar water solubility of a methyl-alkyl ether anesthetic compound; and b) selecting the compound as a candidate anesthetic if the compound has a molar water solubility above about 2.4 mM and below about 11 mM, wherein the candidate anesthetic selectively potentiates $GABA_A$ receptors and does not inhibit NMDA receptors. More preferably, the molar water solubility is below about 10 mM, including below about 9 mM, including below about 8 mM, including below about 7 mM, and including below about 6 mM.

In a related aspect, the invention provides methods of selecting methyl-alkyl ether anesthetic that both potentiates $GABA_A$ receptors and inhibits NMDA receptors, the method comprising: a) determining a molar water solubility of a methyl-alkyl ether anesthetic compound; and b) selecting the compound as a candidate anesthetic if the compound has a molar water solubility above about 5.7 mM and below about 100 mM, wherein the candidate anesthetic both potentiates $GABA_A$ receptors and inhibits NMDA receptors More preferably, the molar water solubility is below about 75 mM, including below about 50 mM, including below about 40 mM, including below about 30 mM, and including below about 20 mM, and is more than about 6 mM, including more than about 7 mM, including more than about 8 mM, including more than about 9 mM, and including more than about 10 mM.

In a further aspect, the present invention provides compositions comprising a compound or a mixture of compounds used in the above and herein described methods, wherein the composition is formulated for inhalational or pulmonary delivery of the compound or mixture of compounds. In certain embodiments, the compound or mixture of compounds is vaporized into or directly mixed or diluted with a carrier gas, e.g., oxygen, air, or helium, or a mixture thereof. As such, in particular embodiments, the compositions of the present invention comprise a compound or a mixture of compounds described herein in admixture with a carrier gas (e.g., oxygen, air, and/or helium) for inhalational or pulmonary delivery.

Other objects, features, and advantages of the present invention will be apparent to one of skill in the art from the following detailed description.

Definitions

The term "inhalational anesthetic" refers to gases or vapors that possess anesthetic qualities that are administered by breathing through an anesthesia mask or ET tube connected to an anesthetic machine. In addition to any of the dialkyl ethers disclosed herein, some currently used inhalational anesthetics include without limitation volatile anesthetics (for example, halothane, isoflurane, sevoflurane and desflurane) and the gases ethylene, nitrous oxide and xenon.

The term "injectable anesthetic or sedative drug" refers to anesthetics or sedatives that can be injected under the skin via a hypodermic needle and syringe and that through actions on nerves in the brain or spinal cord can either render an individual insensible to painful stimuli, or decrease an individual's perceived sensation of painful stimuli, or induce within an individual an amnestic and/or calming effect.

The term "anesthetic-sensitive receptor" refers to a cell membrane protein that binds to an anesthetic agent and whose function is modulated by the binding of that anesthetic agent. Anesthetic-sensitive receptors are usually ion channels or cell membrane that are indirectly linked to ion channels via second messenger systems (such as G-proteins and tyrosine kinases) and can have 2, 3, 4, or 7 transmembrane regions. Such receptors can be comprised of 2 or more subunits and function as part of a protein complex. Activation or inhibition of these receptors results in either a direct change in ion permeability across the cell membrane that alters the cell resting membrane potential, or alters the response of the cell receptor to its endogenous ligand in such a way that the change in ion permeability and cell membrane potential normally elicited by the endogenous ligand is changed. Exemplary anesthetic-sensitive receptors include gamma-aminobutyric acid (GABA) receptors, N-methyl-D-aspartate (NMDA) receptors, voltage-gated sodium ion channels, voltage-gated potassium ion channels, two-pore domain potassium channels, adrenergic receptors, acetylcholine receptors, glycine and opioid receptors.

The term "effective amount" or "pharmaceutically effective amount" refers to the amount and/or dosage, and/or dosage regime of one or more compounds necessary to bring about the desired result e.g., an amount sufficient to effect anesthesia, render the subject unconscious and/or immobilize the subject.

As used herein, the term "pharmaceutically acceptable" refers to a material, such as a carrier or diluent, which does not abrogate the biological activity or properties of the compound useful within the invention, and is relatively non-toxic, i.e., the material may be administered to an individual without causing undesirable biological effects or interacting in a deleterious manner with any of the components of the composition in which it is contained.

As used herein, the term "composition" or "pharmaceutical composition" refers to a mixture of at least one compound useful within the invention with a pharmaceutically acceptable carrier. The pharmaceutical composition facilitates administration of the compound to a subject.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The terms "patient," "individual," and "subject" interchangeably refer to any mammal, e.g., a human or non-human mammal, e.g., a non-human primate, a domesticated mammal (e.g., canine, feline), an agricultural mammal (e.g., equine, bovine, ovine, porcine), or a laboratory mammal (e.g., *rattus*, murine, *lagomorpha*, hamster).

BRIEF DESCRIPTION OF THE DRAWINGS

None

DETAILED DESCRIPTION OF THE INVENTION

I. Ether Compounds, Compositions and Methods of Use

In one aspect, the present invention provides methods of inducing anesthesia in a subject comprising administering to the subject via the respiratory system an effective amount of a halogenated ether compound or a mixture of halogenated ether compounds including, but not limited to, halogenated methyl-ethyl ethers, halogenated methyl-isopropyl ethers, and halogenated methyl-propyl ethers.

In some embodiments, the halogenated methyl-ethyl ether is selected from the group consisting of: Ethane, 1-(chlorodifluoromethoxy)-1,1,2,2,2-pentafluoro- (CAS #276640-96-1); Ethane, 2-bromo-1,1,1-trifluoro-2-(trifluoromethoxy)- (CAS #84011-04-1); Ethane, 1-bromo-1,2,2-trifluoro-1-(trifluoromethoxy)- (CAS #885275-60-5); Ethane, 2-bromo-1,1,2-trifluoro-1-(trifluoromethoxy)- (CAS #84011-03-0); Ethane, 1-bromo-1,1,2-trifluoro-2-(trifluoromethoxy)- (CAS #2356-55-0); Ethane, 2-chloro-1,1,2-trifluoro-1-(trifluoromethoxy)- (CAS #879885-11-7); Ethane, 2-chloro-1,1,1-trifluoro-2-(trifluoromethoxy)- (CAS #94720-92-0); Ethane, 1-chloro-1,1,2-trifluoro-2-(trifluoromethoxy)- (CAS #2356-59-4); Ethane, 1-chloro-1,1-difluoro-2-(trifluoromethoxy)-(CAS #1645-80-3); Ethane, 1-chloro-1,2-difluoro-2-(trifluoromethoxy)-, (R*,S*)-(9CI) (CAS #84011-29-0); Ethane, 1-chloro-1,2-difluoro-2-(trifluoromethoxy)-, (R*,R*)-(9CI) (CAS #84011-28-9); Ethane, 1-chloro-1,2-difluoro-2-(trifluoromethoxy)- (CAS #54362-39-9); Ethane, 1-chloro-2,2-difluoro-1-(trifluoromethoxy)- (CAS #33445-33-9); and mixtures thereof.

In an embodiment of the invention, the halogenated methyl-ethyl ether is Ethane, 1-(chlorodifluoromethoxy)-1,1,2,2,2-pentafluoro- (CAS #276640-96-1). In another embodiment of the invention, the halogenated methyl-ethyl ether is Ethane, 2-bromo-1,1,1-trifluoro-2-(trifluoromethoxy)- (CAS #84011-04-1). In an embodiment of the invention, the methyl-ethyl ether is Ethane, 1-bromo-1,2,2-trifluoro-1-(trifluoromethoxy)- (CAS #885275-60-5). In another embodiment of the invention, the methyl-ethyl ether is Ethane, 2-bromo-1,1,2-trifluoro-1-(trifluoromethoxy)- (CAS #84011-03-0). In yet another embodiment of the invention, the methyl-ethyl ether is Ethane, 1-bromo-1,1,2-trifluoro-2-(trifluoromethoxy)-(CAS #2356-55-0). In an embodiment of the invention, the methyl-ethyl ether is Ethane, 2-chloro-1,1,2-trifluoro-1-(trifluoromethoxy)- (CAS #879885-11-7). In another embodiment of the invention, the methyl-ethyl ether is Ethane, 2-chloro-1,1,1-trifluoro-2-(trifluoromethoxy)- (CAS #94720-92-0). In yet another embodiment of the invention, the methyl-ethyl ether is Ethane, 1-chloro-1,1,2-trifluoro-2-(trifluoromethoxy)- (CAS #2356-59-4). In an embodiment of the invention, the methyl-ethyl ether is Ethane, 1-chloro-1,1-difluoro-2-(trifluoromethoxy)- (CAS #1645-80-3). In an embodiment of the invention, the methyl-ethyl ether is Ethane, 1-chloro-1,2-difluoro-2-(trifluoromethoxy)-, (R*,S*)-(9CI) (CAS #84011-29-0). In an embodiment of the invention, the methyl-ethyl ether is Ethane, 1-chloro-1,2-difluoro-2-(trifluoromethoxy)-, (R*,R*)-(9CI) (CAS #84011-28-9). In an embodiment of the invention, the methyl-ethyl ether is Ethane, 1-chloro-1,2-difluoro-2-(trifluoromethoxy)- (CAS #54362-39-9). In an embodiment of the invention, the methyl-ethyl ether is Ethane, 1-chloro-2,2-difluoro-1-(trifluoromethoxy)- (CAS #33445-33-9).

In other embodiments, the halogenated methyl-isopropyl ether is selected from the group consisting of: Propane, 1-chloro-1,1,2,3,3,3-hexafluoro-2-(trifluoromethoxy)- (CAS #41255-97-4); Propane, 1,1,1,2,3,3,3-heptafluoro-2-(trifluoromethoxy)- (CAS #60901-74-8); Propane, 1,1,1,3,3,3-hexafluoro-2-(trifluoromethoxy)- (CAS #162401-05-0); Propane, 2-(difluoromethoxy)-1,1,1,2,3,3,3-heptafluoro- (CAS #57041-60-8); Propane, 1,1,1,2,3,3,3-heptafluoro-2-(fluoromethoxy)- (CAS #57041-59-5); Propane, 2-(difluoromethoxy)-1,1,1,3,3,3-hexafluoro- (CAS #26103-08-2); Propane, 2-(difluoromethoxy)-1,1,1,2,3,3-hexafluoro- (CAS #233258-12-3); Propane, 1,1,1,2,3,3,3-heptafluoro-2-methoxy- (CAS #22052-84-2); Propane, 1,1,1,3,3,3-hexafluoro-2-methoxy- (CAS #13171-18-1); Propane, 1,1,2-trifluoro-2-(trifluoromethoxy)- (CAS #1219442-00-8); Propane, 2-(difluoromethoxy)-1,1,1,2-tetrafluoro- (CAS #32793-57-0); and mixtures thereof.

In an embodiment of the invention, the halogenated methyl-isopropyl ether is Propane, 1-chloro-1,1,2,3,3,3-hexafluoro-2-(trifluoromethoxy)- (CAS #41255-97-4). In another embodiment of the invention, the methyl-isopropyl ether is Propane, 1,1,1,2,3,3,3-heptafluoro-2-(trifluoromethoxy)- (CAS #60901-74-8). In an embodiment of the invention, the methyl-isopropyl ether is Propane, 1,1,1,3,3,3-hexafluoro-2-(trifluoromethoxy)- (CAS #162401-05-0). In yet another embodiment of the invention, the methyl-isopropyl ether is Propane, 2-(difluoromethoxy)-1,1,1,2,3,3,3-heptafluoro- (CAS #57041-60-8). In an embodiment of the invention, the methyl-isopropyl ether is Propane, 1,1,1,2,3,3,3-heptafluoro-2-(fluoromethoxy)- (CAS #57041-59-5). In another embodiment of the invention, the methyl-isopropyl ether is Propane, 2-(difluoromethoxy)-1,1,1,3,3,3-hexafluoro- (CAS #26103-08-2). In yet another embodiment of the invention, the methyl-isopropyl ether is Propane, 2-(difluoromethoxy)-1,1,1,2,3,3-hexafluoro- (CAS #233258-12-3). In an embodiment of the invention, the methyl-isopropyl ether is Propane, 1,1,1,2,3,3,3-heptafluoro-2-methoxy- (CAS #22052-84-2). In yet another embodiment of the invention, the methyl-isopropyl ether is Propane, 1,1,1,3,3,3-hexafluoro-2-methoxy- (CAS #13171-18-1). In a further embodiment of the invention, the methyl-isopropyl ether is Propane, 1,1,2-trifluoro-2-(trifluoromethoxy)- (CAS #1219442-00-8). In another embodiment of the invention, the methyl-isopropyl ether is Propane, 2-(difluoromethoxy)-1,1,1,2-tetrafluoro-(CAS #32793-57-0).

In further embodiments, the halogenated methyl-propyl ether is selected from the group consisting of: Propane, 1,1,2,2,3,3-hexafluoro-1-methoxy- (CAS #160620-20-2); Propane, 1,1,1,2,2,3-hexafluoro-3-methoxy- (CAS #123202-00-6); Propane, 1,1,1,2,3,3-hexafluoro-3-(fluoromethoxy)- (CAS #60598-14-3); Propane, 3-(difluoromethoxy)-1,1,1,2,2-pentafluoro- (CAS #56860-81-2); Propane, 1,1,1,2,2-pentafluoro-3-(fluoromethoxy)- (CAS #1515-13-5); and mixtures thereof.

In an embodiment of the invention, the halogenated methyl-propyl ether is Propane, 1,1,2,2,3,3-hexafluoro-1-methoxy- (CAS #160620-20-2). In an embodiment of the invention, the halogenated methyl-propyl ether is Propane, 1,1,1,2,2,3-hexafluoro-3-methoxy- (CAS #123202-00-6); Propane, 1,1,1,2,3,3-hexafluoro-3-(fluoromethoxy)- (CAS #60598-14-3). In yet another embodiment of the invention, the halogenated methyl-propyl ether is Propane, 3-(difluoromethoxy)-1,1,1,2,2-pentafluoro- (CAS #56860-81-2). In another embodiment of the invention, the halogenated methyl-propyl ether is Propane, 1,1,1,2,2-pentafluoro-3-(fluoromethoxy)- (CAS #1515-13-5).

In a further aspect, the present invention provides compositions comprising an ether compound or a mixture of ether compounds used in the methods described herein, wherein the composition is formulated for inhalational or pulmonary delivery of the ether compound or mixture of ether compounds.

Tables 2-4, following the last page of the description, list the Chemical Abstracts Service (CAS) registry numbers, calculated Molar Water Solubilities (MWS) and standard Vapor Pressure (VP) (at 25° C.) of compounds listed above. MWS can be predicted or calculated using Advanced Chemistry Development (ACD/Labs) Software, as molar water solubility in pure water at pH=7 and 20° C., as reported in SciFinder. Table 2 lists methyl-ethyl ethers, Table 3 lists methyl-isopropyl ethers, and Table 4 lists methyl-propyl ethers.

An upper limit cut-off value and a lower limit cut-off value have been defined for calculated molar water solubilities of halogenated ether compounds associated with modulation of NMDA receptors, and with a lack of NMDA receptor modulation, respectively. Methyl-isopropyl ether 1,1,1,2,3,3,3-heptafluoro-2-methoxy-propane (CAS #22052-84-2) has a calculated molar water solubility of 11 mM and inhibits NMDA receptors at a saturated aqueous phase concentration; this represents the lowest molar water solubility, that has been studied, that still modulates NMDA receptors. The methyl-ethyl ether 1-bromo-1,1,2-trifluoro-2-(trifluoromethoxy)-ethane (CAS #2356-55-0) has a molar water solubility of 5.7 mM and does not modulate NMDA receptors at a saturated aqueous phase concentration, and represents the highest molar water solubility, that has been studied, that does not modulate NMDA receptors. All halogenated methyl-alkyl ether compounds having a calculated molar water solubility equal or greater than 11 mM are expected to modulate both NMDA receptors and $GABA_A$ receptors at saturated aqueous phase concentrations. All halogenated methyl-alkyl ether compounds with a calculated molar water solubility equal or less than 5.7 mM do not modulate/inhibit NMDA receptors. Consequently, a halogenated methyl-alkyl ether compound having a calculated molar water solubility greater than 5.7 mM but less than 11 mM may or may not modulate NMDA receptor function, and such targeted compounds can be independently tested.

A methyl-ethyl ether compound with a calculated molar water solubility of less than 2.4 mM has a small degree of $GABA_A$ modulation that is of insufficient magnitude to be an effective general anesthetic. The methyl-ethyl ether compounds of the present invention preferably have a calculated molar water solubility of at least 2.4 mM or more.

A compound of the present invention preferably has a saline-gas partition coefficient suitable for desirable pharmacokinetics as an inhaled anaesthetic. The saline-gas partition coefficient for a compound of interest can be measured by gas chromatography using the headspace exchange technique described in Soares J H, Brosnan R J, Fukushima F B, Hodges J, Liu H: Solubility of haloether anesthetics in human and animal blood. Anesthesiology 2012; 117: 48-55, the disclosure of which is incorporated by reference in its entirety. Generally, compounds having a lower saline-gas partition coefficient have more desirable pharmacokinetics, while compounds having a higher saline-gas partition coefficient have less desirable pharmacokinetics. For example, a halogenated methyl-ethyl ether compound having both a higher molar water solubility and lower vapor pressure than desflurane (a conventional halogenated methyl-ethyl ether) will have a higher predicted saline-gas partition coefficient than desflurane, and thus, less desirable pharmacokinetics as compared to desflurane. Likewise, a halogenated methyl-isopropyl ether compound having both a higher molar water solubility and lower vapor pressure than sevoflurane (a conventional halogenated methyl-isopropyl ether) will have a higher predicted saline-gas partition coefficient than sevoflurane, and thus, less desirable pharmacokinetics as compared to sevoflurane.

Some of the compounds set forth herein include chiral centers. Chiral centers generally refer to a carbon atom that is attached to four unique substituents. With respect to these chiral-center containing compounds, the present invention provides for methods that include the use of, and administration of, these chiral-center containing compounds as either pure entantiomers, as mixtures of enantiomers, as well as mixtures of diastereoisomers or as a purified diastereomer. In some embodiments, the R configuration of a particular enantiomer is preferred for a particular method. In yet other embodiments, the S configuration of a particular enantiomer is preferred for a particular method. The present invention includes methods of administering racemic mixtures of compounds having chiral centers. The present invention includes methods of administering one particular stereoisomer of a compound. In certain embodiments, a particular ratio of one enantiomer to another enantiomer is preferred for use with a method described herein. In other embodiments, a particular ratio of one diastereomer to other diastereomers is preferred for use with a method described herein.

In some embodiments, the ether compounds described herein are useful as inhaled sedatives, inhaled tranquilizers, inhaled analgesics, and/or inhaled hypnotics.

Halogenated methyl-alkyl ether compounds as effective anaesthetics according to the present invention have a standard vapor pressure of 0.1 atm (76 mm Hg) or more at 25° C., a property important to the volatilizing of a compound for inhalational delivery. A halogenated ether compound according to the present invention also has a number of halogen atoms (X, where X=F, Cl, or Br) that exceeds the number of hydrogen atoms.

II. Subjects Who May Benefit

The anesthetic compounds and methods described herein find use for inducing anesthesia in any subject in need thereof. For example, the subject may be undergoing a surgical procedure that requires the induction of temporary unconsciousness and/or immobility.

The anesthetic compounds and methods described herein also find use for inducing sedation in any subject in need thereof. For example, the subject may be undergoing a surgical procedure that requires a reduction in the patient's anxiety or the induction of a temporary calm or tranquil state in the subject.

The patient receiving the anesthetic may have been selected for having or at risk of having a sensitivity or adverse reaction to an anesthetic that activates a particular anesthetic-sensitive receptor or subset of anesthetic-receptors. For example, the patient may have or be at risk of having a sensitivity or adverse reaction to an anesthetic that activates one or more of NMDA receptors, two-pore potassium channels, voltage-gated ion channels, $GABA_A$ receptors, glycine receptors, or another anesthetic-sensitive receptor. In such cases, the anesthetic administered to the patient has a water solubility that is less than the solubility threshold concentration for the receptor for which it is sought to avoid modulating.

In various embodiments, it may be desirable to induce in the subject amnesia and/or immobility by potentiating $GABA_A$ receptors, but minimize or avoid inducing possible respiratory or neurologic side-effects that may be associated with inhibition of NMDA receptors.

III. Formulations and Methods of Administration a. Formulations

The present invention also encompasses the use of pharmaceutical compositions comprising an ether compound or a mixture of ether compounds as described herein to induce anesthesia in a subject.

The present invention also encompasses the use of pharmaceutical compositions comprising an ether compound or a mixture of ether compounds as described herein to induce sedation in a subject.

Such a pharmaceutical composition may consist of at least one compound of the present invention, in a form suitable for administration to a subject, or the pharmaceutical composition may comprise at least one compound of the present invention, and one or more pharmaceutically acceptable carriers, one or more additional ingredients, or some combination of these.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

As used herein, the term "pharmaceutically acceptable carrier" means a pharmaceutically acceptable material, composition or carrier, such as a carrier gas, a liquid or solid filler, stabilizer, dispersing agent, suspending agent, diluent, excipient, thickening agent, solvent or encapsulating material, involved in carrying or transporting a compound of the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound of the invention, and not injurious to the subject. Non-limiting examples of carrier gases include oxygen, air, helium, nitrous oxide, xenon, and mixtures thereof. Other examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound of the invention, and are physiologically acceptable to the subject. Supplementary active compounds may also be incorporated into the compositions. Other additional ingredients that may be included in the pharmaceutical compositions used in the practice of the invention are known in the art and described, for example in Remington: The Science and Practice of Pharmacy (Remington: The Science & Practice of Pharmacy), $21^{st}$ Edition, 2011, Pharmaceutical Press, and Ansel's Pharmaceutical Dosage Forms and Drug Delivery Systems, Allen, et al., eds., $9^{th}$ Edition, 2010, Lippincott Williams & Wilkins, which are incorporated herein by reference.

In various embodiments, the compounds are formulated for delivery via a respiratory pathway, e.g., suitably developed for inhalational, pulmonary, intranasal, delivery. In various embodiments, the compound or mixture of compounds is vaporized into or directly mixed or diluted with a carrier gas, e.g., oxygen, air, or helium, or a mixture thereof. A preservative may be further included in the vaporized formulations, as appropriate. Other contemplated formulations include projected nanoparticles, and liposomal preparations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals including agricultural mammals (e.g., cattle, pigs, horses, sheep), domesticated mammals (e.g., cats, and dogs), and laboratory mammals (e.g., rats, mice, rabbits, hamsters).

b. Administration

In some embodiments, the methods further comprise administering the selected anesthetic (e.g., an ether compound or mixture of ether compounds as described herein) to a patient. The anesthetic can be administered by any route sufficient to achieve a desired anesthetic, amnestic, analgesic, and/or sedative effect. For example, the anesthetic can be administered intravenously, inhalationally, subcutaneously, intramuscularly, transdermally, topically, or by any other route to achieve an efficacious effect.

The anesthetic is administered at a dose sufficient to achieve a desired anesthetic endpoint, for example, a state of insensitivity to noxious stimulation (also referred to as "general anesthesia"), immobility, amnesia, analgesia, unconsciousness, sedation, and/or autonomic quiescence.

Administered dosages for anesthetic agents are in accordance with dosages and scheduling regimens practiced by those of skill in the art. General guidance for appropriate dosages of pharmacological agents used in the present methods is provided in *Goodman and Gilman's The Pharmacological Basis of Therapeutics,* 12th Edition, 2010, supra, and in a Physicians' Desk Reference (PDR), for example, in the 65th (2011) or 66th (2012) Eds., PDR Network, each of which is hereby incorporated herein by reference.

The appropriate dosage of anesthetic agents will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

Determination of an effective amount is well within the capability of those skilled in the art, especially in light of the detailed disclosure provided herein. Generally, an efficacious or effective amount of a combination of one or more anesthetic agents is determined by first administering a low dose or small amount of the anesthetic, and then incrementally increasing the administered dose or dosages, adding a second or third medication as needed, until a desired effect is observed in the treated subject with minimal or no toxic side effects. Applicable methods for determining an appropriate dose and dosing schedule for administration of anesthetics are described, for example, in *Goodman and Gilman's The Pharmacological Basis of Therapeutics,* 12th Edition, 2010, supra; in a Physicians' Desk Reference (PDR), supra; in *Remington: The Science and Practice of Pharmacy (Remington: The Science & Practice of Pharmacy),* 21st Edition, 2011, Pharmaceutical Press, and *Ansel's Pharmaceutical Dosage Forms and Drug Delivery Systems,* Allen, et al., eds., 9th Edition, 2010, Lippincott Williams & Wilkins; and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

Dosage amount and interval can be adjusted individually to provide plasma levels of the active compounds which are sufficient to maintain a desired therapeutic effect. Preferably, therapeutically effective serum levels will be achieved by administering a single dose, but efficacious multiple dose schedules are included in the invention. In cases of local administration or selective uptake, the effective local concentration of the drug may not be related to plasma concentration. One having skill in the art will be able to optimize therapeutically effective local dosages without undue experimentation.

The dosing of analog compounds can be based on the parent compound, at least as a starting point.

In various embodiments, the compositions are delivered to the subject via a respiratory pathway, e.g., via inhalational, pulmonary and/or intranasal delivery. Technologies and devices for inhalational anesthetic drug dosing are known in the art and described, e.g., in MILLER'S ANESTHESIA, Edited by Ronald D. Miller, et al., 2 vols, 7th ed, Philadelphia, Pa., Churchill Livingstone/Elsevier, 2010; and Meyer, et al., *Handb Exp Pharmacol.* (2008) (182):451-70. In one embodiment, the pharmaceutical compositions useful for inducing anesthesia can be administered to deliver a dose of between about 0.1-10.0 percent of 1 atmosphere (1 atm), e.g., about 0.5-5.0 percent of 1 atm, e.g., about 1.0-3.5 percent of 1 atm, e.g., about 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10.0 percent of 1 atm, e.g., delivered over the period of time of desired anesthesia. In another embodiment, the pharmaceutical compositions useful for inducing anesthesia can be administered to deliver a dose of greater than about 10.0 percent of 1 atmosphere (1 atm), e.g., about 10.0-50.0 percent of 1 atm, e.g., about 10.0-25.0 percent of 1 atm, e.g., about 10.0, 15.0, 20.0, 25.0, 30.0, 35.0, 40.0, 45.0, or 50.0 percent of 1 atm, e.g., delivered over the period of time of desired anesthesia. The dose used will be dependent upon the drug potency, and the compound or mixture of compounds administered.

Detailed information about the delivery of therapeutically active agents in the form of vapors or gases is available in the art. The compound will typically be vaporized using a vaporizer using a carrier gas such as oxygen, air, or helium, or a mixture thereof, to achieve a desired drug concentration suitable for inhalation by use of a semi-open or semi-closed anesthetic circuit, as is known to individuals familiar with the art of anesthesia. The compound in a gaseous form may also be directly mixed with a carrier gas such as oxygen, air, or helium, or a mixture thereof, to achieve a desired drug concentration suitable for inhalation by use of a semi-open or semi-closed anesthetic circuit, as is known to individuals familiar with the art of anesthesia. The drug may also be administered by direct application of onto or through a breathing mask, also termed an open circuit, as is known to individuals familiar with the art of anesthesia. In animals, the drug may also be administered into a closed chamber or container containing the animal subject whereby the drug is delivered by the respiratory tract as the animal breathes, as is known to individuals familiar with animal anesthesia.

In some aspects of the present invention, the anesthetic compound or mixture of compounds is dissolved or suspended in a suitable solvent, such as water, ethanol, or saline, and administered by nebulization. A nebulizer produces an aerosol of fine particles by breaking a fluid into fine droplets and dispersing them into a flowing stream of gas. Medical nebulizers are designed to convert water or aqueous solutions or colloidal suspensions to aerosols of fine, inhalable droplets that can enter the lungs of a patient during inhalation and deposit on the surface of the respiratory airways. Typical pneumatic (compressed gas) medical nebulizers develop approximately 15 to 30 microliters of aerosol per liter of gas in finely divided droplets with volume or mass median diameters in the respirable range of 2 to 4 micrometers. Predominantly, water or saline solutions are used with low solute concentrations, typically ranging from 1.0 to 5.0 mg/mL.

Nebulizers for delivering an aerosolized solution to the lungs are commercially available from a number of sources, including the AERx™ (Aradigm Corp., Hayward, Calif.) and the Acorn II® (Vital Signs Inc., Totowa, N.J.).

Metered dose inhalers are also known and available. Breath actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; and 4,896,832.

In some embodiments, the present invention provides methods for producing analgesia in a subject, comprising administering to the subject via the respiratory system an effective amount of a compound or a mixture of compounds described herein. In some embodiments, the analgesia includes tranquilization. In some embodiments, the analgesia includes sedation. In some embodiments, the analgesia includes amnesia. In some embodiments, the analgesia includes a hypnotic state. In some embodiments, the analgesia includes a state of insensitivity to noxious stimulation.

In some embodiments, the present invention provides methods of producing or inducing tranquilization or sedation in a subject, comprising administering to the subject via the respiratory system an effective amount of a compound or a mixture of compounds described herein. In certain embodiments, the present invention provides methods of producing tranquilization in a subject, comprising administering to the subject via the respiratory system an effective amount of a compound or a mixture of compounds described herein. In some other embodiments, the present invention provides methods of producing amnesia in a subject, comprising administering to the subject via the respiratory system an effective amount of a compound or a mixture of compounds described herein. Typically, the amount of a compound or a mixture of compounds which are described herein that is required to produce amnesia in a subject is larger than the amount required to produce tranquilization in a subject. In yet other embodiments, the present invention provides methods of producing a hypnotic state in a subject, comprising administering to the subject via the respiratory system an effective amount of a compound or a mixture of compounds described herein. Typically, the amount of a compound or a mixture of compounds which are described herein that is required to produce a hypnotic state in a subject is larger than the amount required to produce amnesia in a subject. In still other embodiments, the present invention provides methods of producing a state of insensitivity to noxious stimulation in a subject, comprising administering to the subject via the respiratory system an effective amount of a compound or a mixture of compounds described herein. Typically, the amount of a compound or a mixture of compounds which are described herein that is required to produce a state of insensitivity to noxious stimulation in a subject is larger than the amount required to produce a hypnotic state in a subject.

The present invention includes methods of inducing a spectrum of states of anesthesia in a subject as a function of the administered dosage of a compound or a mixture of compounds described herein. In some embodiments, the methods include administering low dosages of a compound or a mixture of compounds described herein to induce tranquilization or sedation in a subject. In other embodiments, the methods include administering higher dosages than that required to induce tranquilization of a compound or a mixture of compounds described herein to induce amnesia in a subject. In yet other embodiments, the methods include administering even higher dosages than that required to induce amnesia in a subject of a compound or a mixture of compounds which are described herein to induce a hypnotic state in a subject. In still other embodiments, the methods include administering yet even higher dosages than that required to induce a hypnotic state in a subject of a compound or a mixture of compounds which are described herein to induce a state of insensitivity to noxious stimulation in a subject, also known as "general anesthesia".

EXAMPLE

The following example is offered to illustrate, but not to limit the claimed invention.

Example 1. 1-bromo-1,1,2-trifluoro-2-(trifluoromethoxy)-ethane (CAS #2356-55-0) Induces Anesthesia In a method to measure the minimum alveolar concentration (MAC) for Loss Of Righting Reflex ($MAC_{LORR}$), for assessing the performance of a compound as a general anesthetic, mice were placed in a 3.5 cm diameter, 14.5 cm long acrylic cylinder connected on either end via unidirectional valves to a closed microcircuit containing a carbon dioxide absorbent vessel, latex balloon breathing bag, sampling port, and 100 mL glass syringe-driven piston. The $MAC_{LORR}$ is a measure of the anesthetic $ED_{50}$ required to prevent loss-of-righting reflex in 50% of individuals. The procedures for measuring $MAC_{LORR}$ and MAC, as well as general methods for measuring agent concentrations by gas chromatography, have been described in Deady J E, Koblin D D, Eger E I, 2nd, Heavner J E, D'Aoust B: Anesthetic potencies and the unitary theory of narcosis. Anesth Analg 1981; 60: 380-4; Brosnan R J, Thiesen R: Increased NMDA receptor inhibition at an increased Sevoflurane MAC. BMC Anesthesiol 2012; 12: 9; and Brosnan R J: GABA(A) receptor antagonism increases NMDA receptor inhibition by isoflurane at a minimum alveolar concentration. Vet Anaesth Analg 2011; 38: 231-9, the disclosures of which are incorporated by reference in their entireties.

The methyl-ethyl ether 1-bromo-1,1,2-trifluoro-2-(trifluoromethoxy)-ethane (CAS #2356-55-0) was found to be devoid of NMDA receptor effects and produced general anesthesia in mice.

Other ether compounds including those compounds described herein are also suitable anesthetics with increased receptor specificity (e.g., the compound potentiates $GABA_A$ receptors, but does not inhibit NMDA receptors).

It is understood that the examples and embodiments described herein are for illustrative purposes only and that various modifications or changes in light thereof will be suggested to persons skilled in the art and are to be included within the purview of this application and scope of the appended claims. All publications, patents, and patent applications cited herein are hereby incorporated by reference in their entirety for all purposes.

TABLE 2

| Methyl-Ethyl Ethers | CAS | MWS (M) | VP (torr) |
|---|---|---|---|
| Ethane, 1-(chlororodifluoromethoxy)-1,1,2,2,2-pentafluoro- | 276640-96-1 | 4.60E−03 | 907 |
| Ethane, 2-bromo-1,1,1-trifluoro-2-(trifluoromethoxy)- | 84011-04-1 | 5.00E−03 | 277 |
| Ethane, 1-bromo-1,2,2-trifluoro-1-(trifluoromethoxy)- | 885275-60-5 | 5.10E−03 | 206 |
| Ethane, 2-bromo-1,1,2-trifluoro-1-(trifluoromethoxy)- | 84011-03-0 | 5.50E−03 | 212 |
| Ethane, 1-bromo-1,1,2-trifluoro-2-(trifluoromethoxy)- | 2356-55-0 | 5.70E−03 | 202 |
| Ethane, 2-chloro-1,1,2-trifluoro-1-(trifluoromethoxy)- | 879885-11-7 | 1.00E−02 | 626 |
| Ethane, 2-chloro-1,1,1-trifluoro-2-(trifluoromethoxy)- | 94720-92-0 | 1.10E−02 | 648 |
| Ethane, 1-chloro-2-(difluoromethoxy)-1,1,2,2-tetrafluoro- | 32778-12-4 | 1.10E−02 | 465 |
| Ethane, 1-chloro-1,1,2-trifluoro-2-(trifluoromethoxy)- | 2356-59-4 | 1.10E−02 | 615 |
| Ethane, 1-chloro-1-(difluoromethoxy)-1,2,2,2-tetrafluoro- | 57041-64-2 | 1.20E−02 | 427 |
| Ethane, 2-chlorodifluoromethoxy)-1,1,1,2-tetrafluoro- | 172103-16-1 | 1.40E−02 | 474 |
| Ethane, 2-(chlorodifluoromethoxy)-1,1,1,2-tetrafluoro, (S)- (9CI) | 167072-93-7 | 1.40E−02 | 474 |
| Ethane, 2-(chlorodifluoromethoxy)-1,1,1,2-tetrafluoro-, (R)- (9CI) | 161893-84-1 | 1.40E−02 | 474 |
| Ethane, 1-(chlorodifluoromethoxy)-1,1,2,2-tetrafluoro- | 37031-51-9 | 1.40E−02 | 420 |
| Ethane, 2-chloro-1,1-difluoro-1-(trifluoromethoxy)- | 25957-33-9 | 2.20E−02 | 598 |
| Ethane, 1-chloro-1,1,2,2-tetrafluoro-2-(fluoromethoxy)- | 53997-65-2 | 2.50E−02 | 319 |
| Ethane, 1-chloro-1,1-difluoro-2-(trifluoromethoxy)- | 1645-80-3 | 2.60E−02 | 575 |
| Ethane, 1-chloro-1,2-difluoro-2-(trifluoromethoxy)-, (R*,S*)- (9CI) | 84011-29-0 | 2.90E−02 | 330 |
| Ethane, 1-chloro-1,2-difluoro-2-(trifluoromethoxy)-, (R*,R*)- (9CI) | 84011-28-9 | 2.90E−02 | 330 |
| Ethane, 1-chloro-1,2-difluoro-2-(trifluoromethoxy)- | 54362-39-9 | 2.90E−02 | 330 |
| Ethane, 1-chloro-2,2-difluoro-1-(trifluoromethoxy)- | 33445-33-9 | 3.00E−02 | 301 |
| Ethane, 2-(chlorodifluoromethoxy)-1,1,1-trifluoro- | 33018-78-9 | 3.00E−02 | 458 |

TABLE 3

| Methyl-Isopropyl Ethers | CAS | MWS (M) | VP (torr) |
|---|---|---|---|
| Propane, 1-chloro-1,1,2,3,3,3-hexafluoro-2-(trifluoromethoxy)- | 41255-97-4 | 4.40E−04 | 328 |
| Propane, 1,1,1,2,3,3,3-heptafluoro-2-(trifluoromethoxy)- | 60901-74-8 | 6.60E−04 | 1370 |
| Propane, 1,1,1,3,3,3-hexafluoro-2-(trifluoromethoxy)- | 162401-05-0 | 2.10E−03 | 1050 |
| Propane, 2-(difluoromethoxy)-1,1,1,2,3,3,3-heptafluoro- | 57041-60-8 | 2.30E−03 | 615 |
| Propane, 1,1,1,2,3,3,3-heptafluoro-2-(fluoromethoxy)- | 57041-59-5 | 5.50E−03 | 451 |
| Propane, 2-(difluoromethoxy)-1,1,1,3,3,3-hexafluoro- | 26103-08-2 | 6.60E−03 | 441 |
| Propane, 2-(difluoromethoxy)-1,1,1,2,3,3-hexafluoro- | 233258-12-3 | 6.90E−03 | 272 |
| Propane, 1,1,1,2,3,3,3-heptafluoro-2-methoxy- | 22052-84-2 | 1.10E−02 | 753 |
| Propane, 1,1,1,3,3,3-hexafluoro-2-methoxy- | 13171-18-1 | 2.80E−02 | 537 |
| Propane, 1,1,2-trifluoro-2-(trifluoromethoxy)- | 1219442-00-8 | 2.30E−02 | 614 |
| Propane, 2-(difluoromethoxy)-1,1,1,2-tetrafluoro- | 32793-57-0 | 2.60E−02 | 452 |

TABLE 4

| Methyl-Propyl Ethers | CAS | MWS (M) | VP (torr) |
|---|---|---|---|
| Propane, 1,1,2,2,3,3-hexafluoro-1-methoxy- | 160620-20-2 | 3.10E−02 | 503 |
| Propane, 1,1,1,2,2,3-hexafluoro-3-methoxy- | 123202-00-6 | 2.90E−02 | 726 |
| Propane, 1,1,1,2,3,3-hexafluoro-3-(fluoromethoxy)- | 60598-14-3 | 1.80E−02 | 545 |
| Propane, 3-(difluoromethoxy)-1,1,1,2,2-pentafluoro- | 56860-81-2 | 1.90E−02 | 558 |
| Propane, 1,1,1,2,2-pentafluoro-3-(fluoromethoxy)- | 1515-13-5 | 3.70E−02 | 397 |

What is claimed is:

1. A method for inducing anesthesia in a subject by potentiating $GABA_A$ receptors without inhibiting NMDA receptors, comprising administering to the subject via the respiratory system or via injection, an effective amount of ethane, 1-bromo-1,1,2-trifluoro-2-(trifluoromethoxy)- (CAS #2356-55-0), thereby inducing anesthesia in the subject by potentiating $GABA_A$ receptors without inhibiting NMDA receptors.

2. The method of claim 1, wherein the subject is a mammal.

3. The method of claim 2, wherein the mammal is a human.

4. The method of claim 1, wherein the step of inducing anesthesia includes inducing a state selected from the group consisting of analgesia, tranquilization, sedation, amnesia, a hypnotic state, and a state of insensitivity to noxious stimulation.

5. A method for inducing anesthesia in a subject in need thereof, the method comprising administering to the subject via the respiratory system or via injection, an effective amount of a halogenated methyl-ethyl ether selected from the group consisting of: Ethane, 2-bromo-1,1,1-trifluoro-2-(trifluoromethoxy)- (CAS #84011-04-1); Ethane, 1-bromo-1,2,2-trifluoro-1-(trifluoromethoxy)- (CAS #885275-60-5); Ethane, 2-bromo-1,1,2-trifluoro-1-(trifluoromethoxy)- (CAS #84011-03-0); and Ethane, 1-bromo-1,1,2-trifhioro-2-(trifluoromethoxy)- (CAS #2356-55-0).

6. A method of claim 5, wherein the subject is a mammal.

7. A method of claim 6, wherein the mammal is a human.

8. A method of claim 5, wherein the step of inducing anesthesia includes inducing a state selected from the group consisting of analgesia, tranquilization, sedation, amnesia, a hypnotic state, and a state of insensitivity to noxious stimulation.

9. The method of claim 5, wherein the compound potentiates $GABA_A$ receptors, but does not inhibit NMDA receptors.

10. The method of claim 4, wherein the step of inducing anesthesia induces a state of insensitivity to noxious stimulation.

11. The method of claim 5, wherein the halogenated methyl-ethyl ether is Ethane, 2-bromo-1,1,1-trifluoro-2-(trifluoromethoxy)- (CAS #84011-04-1).

12. The method of claim 11, wherein the step of inducing anesthesia induces a state of insensitivity to noxious stimulation.

13. The method of claim 5, wherein the halogenated methyl-ethyl ether is Ethane, 1-bromo-1,2,2-trifluoro-1-(trifluoromethoxy)- (CAS #885275-60-5).

14. The method of claim 13, wherein the step of inducing anesthesia induces a state of insensitivity to noxious stimulation.

15. The method of claim 5, wherein the halogenated methyl-ethyl ether is Ethane, 2-bromo-1,1,2-trifluoro-1-(trifluoromethoxy)- (CAS #84011-03-0).

16. The method of claim 15, wherein the step of inducing anesthesia induces a state of insensitivity to noxious stimulation.

17. The method of claim 5, wherein the halogenated methyl-ethyl ether is Ethane, 1-bromo-1,1,2-trifhioro-2-(trifluoromethoxy)- (CAS #2356-55-0).

18. The method of claim 17, wherein the step of inducing anesthesia induces a state of insensitivity to noxious stimulation.

* * * * *